United States Patent [19]
Hasson

[11] Patent Number: 5,830,232
[45] Date of Patent: Nov. 3, 1998

[54] DEVICE FOR CLOSING AN OPENING IN TISSUE AND METHOD OF CLOSING A TISSUE OPENING USING THE DEVICE

[76] Inventor: Harrith M. Hasson, 2043 N. Sedgwick, Chicago, Ill. 60614

[21] Appl. No.: 824,699

[22] Filed: Apr. 14, 1997

[51] Int. Cl.⁶ .................................................. A61B 17/04
[52] U.S. Cl. .......................... 606/213; 606/144; 606/148
[58] Field of Search ..................................... 606/232, 144, 606/148, 139, 213

[56] References Cited

U.S. PATENT DOCUMENTS

| | | | |
|---|---|---|---|
| 5,021,059 | 6/1991 | Kensey et al. | 606/213 |
| 5,306,290 | 4/1994 | Martins et al. | 606/232 |
| 5,391,173 | 2/1995 | Wilk | 606/232 |
| 5,413,571 | 5/1995 | Katsaros et al. | 606/213 |
| 5,486,195 | 1/1996 | Myers et al. | 606/213 |
| 5,545,178 | 8/1996 | Kensey et al. | 606/213 |

*Primary Examiner*—Gary Jackson
*Attorney, Agent, or Firm*—Wood, Phillips, VanSanten, Clark & Mortimer

[57] ABSTRACT

A device for facilitating the performance of a medical procedure in a cavity bounded by tissue. The device has a body with a first opening therethrough to define a first passageway for a medical instrument to be directed from externally of the cavity through an opening in the tissue to the cavity and an exposed surface that can be placed against the tissue around the opening therethrough with the device in an operative state relative to the tissue. A second opening is provided through the body to define a second passageway through which a tying instrument can be directed from externally of the tissue through the body and into the cavity bounded by the tissue.

23 Claims, 6 Drawing Sheets

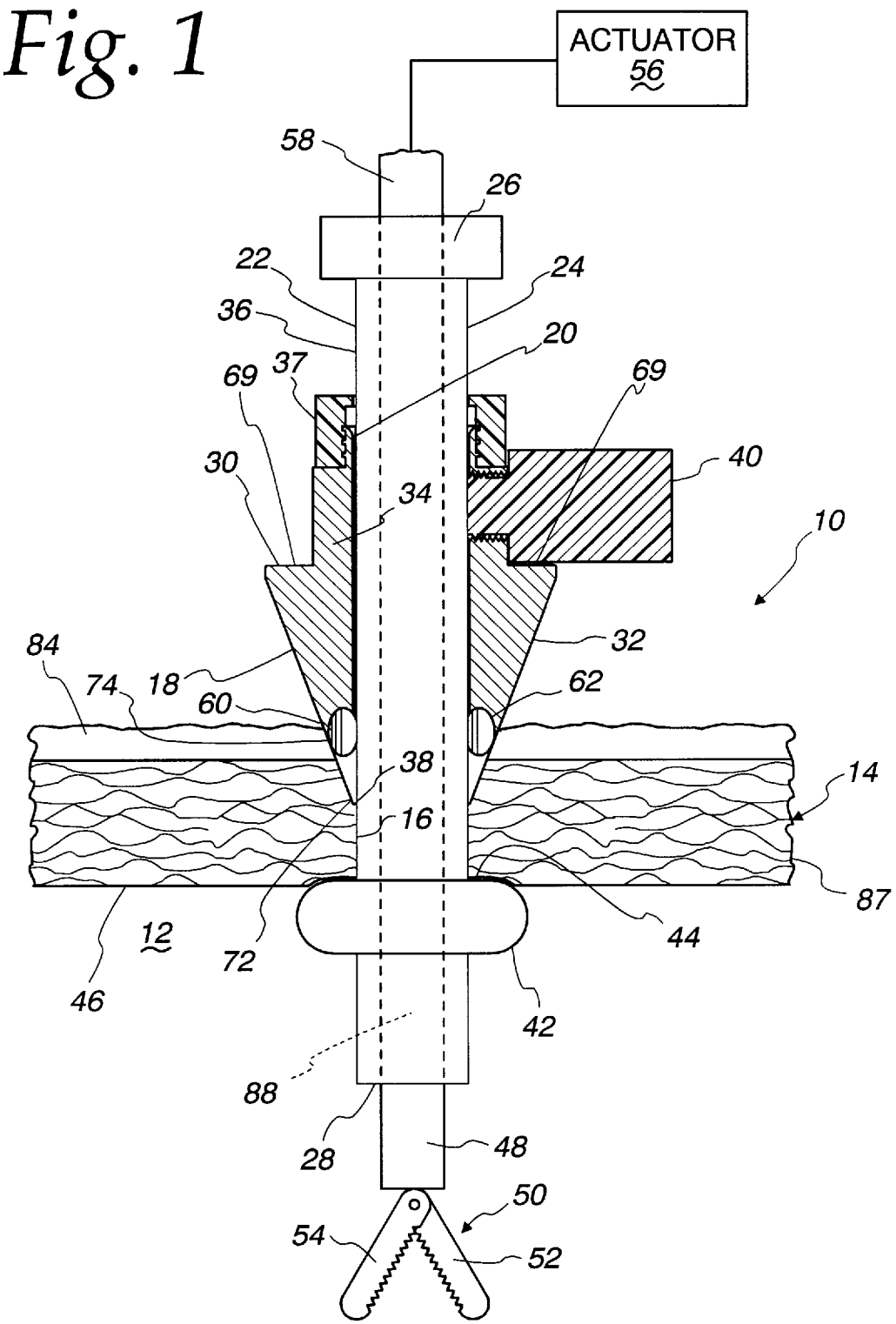

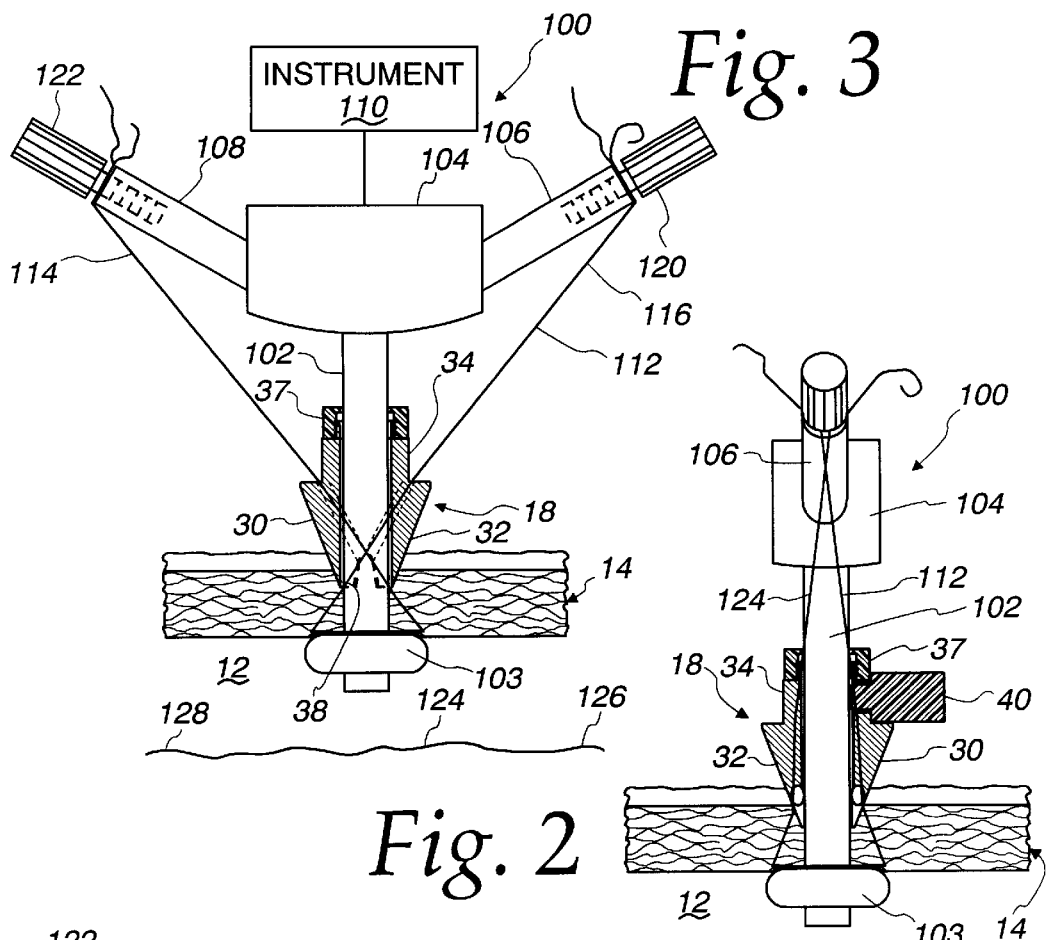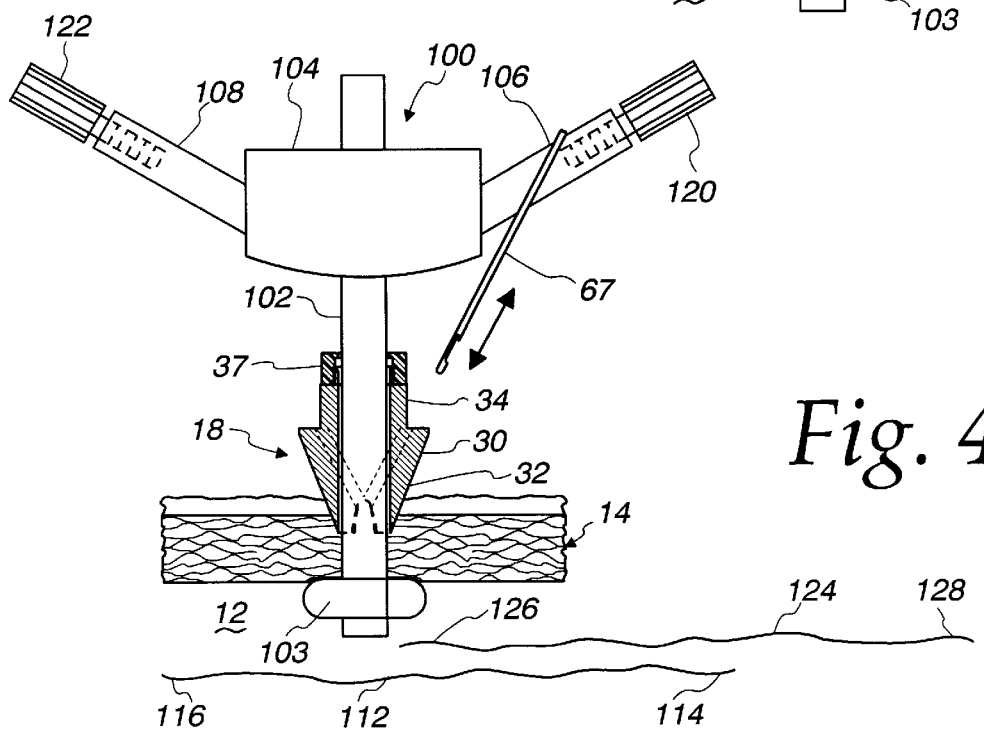

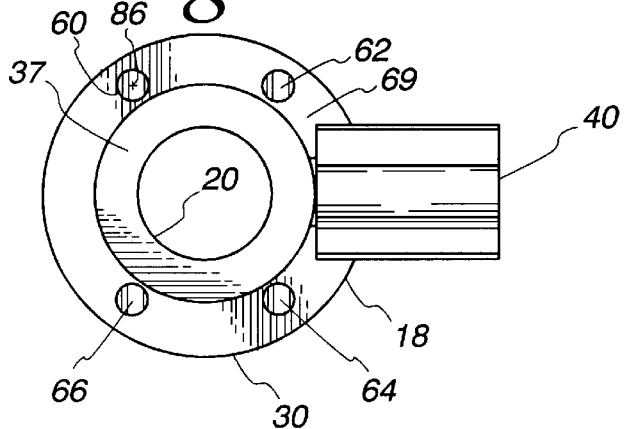
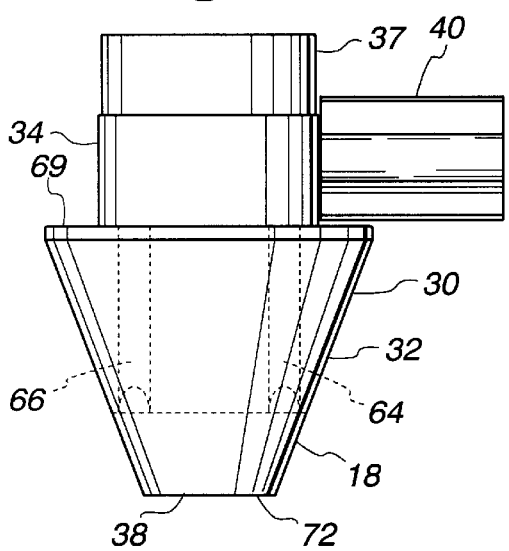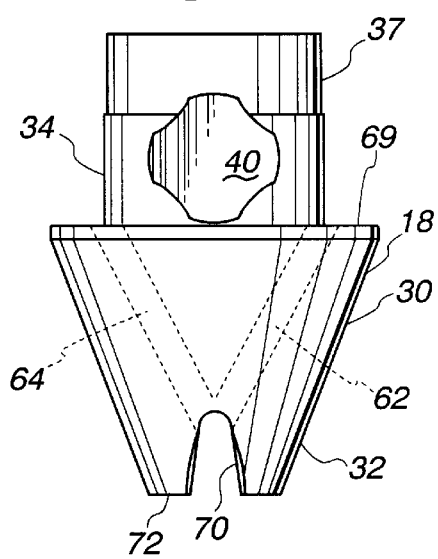
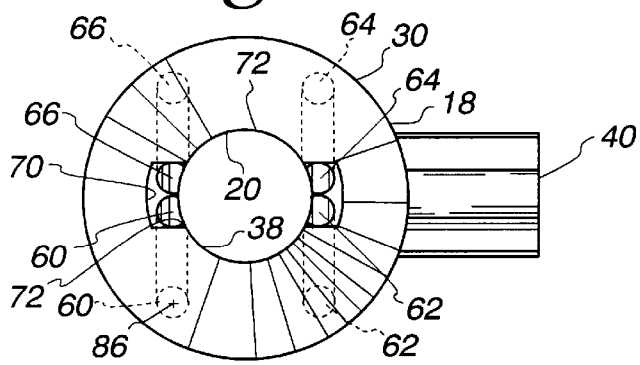

DEVICE FOR CLOSING AN OPENING IN TISSUE AND METHOD OF CLOSING A TISSUE OPENING USING THE DEVICE

BACKGROUND OF THE INVENTION

1. Field of the Invention

This invention relates to medical instruments and procedures and, more particularly, to a medical device that can be used to assist the performance of an internal medical procedure and/or the closing of a tissue opening and a method of using this device.

2. Background Art

Many of the procedures performed by open laparotomy are currently performed by operative laparoscopy. With increased applications of advanced operative laparoscopy, surgeons are experiencing an increased incidence of herniations through laparoscopy sleeved cannula sites. To prevent this complication there is a developing consensus to close the surgical defect associated with the insertion of laparoscopy cannulas 10 mm or greater in outside diameter. Although rare, sliding hernias have been reported with 5 mm laparoscopy cannulas.

Numerous needles and other devices have been developed to accomplish full thickness closure of the abdominal wall at the operative site of cannula insertion. However, the use of such devices has been associated with a certain degree of difficulty. If the device is used while the cannula is still in place, it is cumbersome to introduce the device between the cannula and the skin, because the cannula is tightly apposed to the skin margins of the incision. This is done to penetrate the abdominal wall excluding the skin. Furthermore, obtaining a suitable tissue purchase i.e. further away from the edge of the fascial defect, is technically difficult. On the other hand, if the cannula is tilted within the incision to improve access to the deeper layers of the abdominal wall, the pneumoperitoneum gas escapes rapidly through the less than tight application. Loss of the pneumoperitoneum gas makes the process of penetrating the abdominal wall with a sharp object extremely dangerous; because the bowel becomes quickly situated immediately under the abdominal wall. Therefore, this process has to be accomplished very quickly, without regard to accurate device placement within the abdominal wall.

If the closing device is applied after the laparoscopy cannula has been removed, the pneumoperitoneum gas escapes very rapidly through the open incision precluding any chance of a full thickness closure. Therefore, a device with a plug must be used to seal the incision and maintain the pneumoperitoneum while placing the full-thickness closing sutures.

SUMMARY OF THE INVENTION

In one form of the invention, a device is provided for facilitating the performance of a medical procedure in a cavity bounded by tissue. The device has a body with a first opening therethrough to define a first passageway for a medical instrument to be directed from externally of the cavity through an opening in the tissue to the cavity and an exposed surface that can be placed against the tissue around the opening therethrough with the device in an operative state relative to the tissue. A second opening is provided through the body to define a second passageway through which a tying instrument can be directed from externally of the tissue through the body and into the cavity bounded by the tissue.

In one form, the first and second passageways do not intersect each other.

The above device may be provided in combination with a sleeve which is extended into the first opening in the body.

In one form, the sleeve has an inlet end and an outlet end, with the inlet end of the sleeve residing externally of the tissue and the outlet end of the sleeve residing within the cavity bounded by the tissue with the sleeve and body in a relative operative position and the device in the operative state.

A third opening can be provided through the body to define a third passageway through which a tying instrument can be directed from externally of the tissue through the body and into the cavity bounded by the tissue.

In one form, the first, second and third passageways do not intersect each other.

The second and third passageways each have a vertical axis that may be substantially straight with the central axes of the second and third passageways being non-parallel to each other.

The invention also contemplates the device in combination with a tissue bounding a cavity and having an opening therethrough, wherein the external surface of the body is sealingly placed against a tissue around the tissue opening with the device in the operative state so that the first passageway is aligned with the tissue opening.

Further, a medical instrument can be provided extending from externally of the tissue through the first passageway and the tissue opening into the cavity.

A sleeve may be employed that extends into the first passageway, with the medical instrument extending through the sleeve.

A second instrument with a thread holding portion can be provided, which second instrument extends through the second passageway from externally of the tissue so that the thread holding portion of the second instrument resides within the cavity.

A suturing thread can be provided at least partially in the cavity, with the thread holding portion of the second instrument holding a part of the suturing thread that is in the cavity.

A resilient seal may be provided for the second passageway to block communication of gas from the cavity through the second passageway to externally of the cavity with the second instrument extending through the second passageway.

The invention also contemplates a method of closing an opening through a tissue bounding a cavity, which method includes the steps of: providing a sealing element having a body with an external surface; placing the body of the sealing element against the tissue around the opening in the tissue; directing a first thread into the cavity; drawing a first part of the first thread from the cavity through the body of the sealing element and the tissue to externally of the tissue; and using the first part of the first thread to at least one of a) stabilize the sealing element on the tissue, and b) form a knot to at least partially close the opening in the tissue.

The method may include the step of drawing a second part of the first thread from the cavity through the body of the sealing element and the tissue to externally of the tissue and tying the first and second thread parts together to at least partially close the opening in the tissue.

The invention also contemplates the steps of directing a second thread into the cavity and drawing a first part of the second thread from the cavity through the tissue to externally of the cavity and tying the first part of the first and second threads together to at least partially close the opening in the tissue.

A medical instrument can be provided and directed through a first passageway through the body of the sealing element. The step of drawing the first part of the first thread may include drawing the first part of the first thread through the body of the sealing element through a second passageway in the body of the sealing element that is independent from the first passageway.

The invention further contemplates the step of providing a sleeve that extends into the body of the sealing element to allow a medical instrument to be directed through the sleeve and body of the sealing element into the cavity and the step of drawing a first part of the first thread through the body of the sealing element involves the step of drawing a first part of the first thread through the body of the sealing element without drawing the first thread through the sleeve.

The step of drawing the first part of the first thread through the body of the sealing element may include the steps of providing an instrument with a thread engaging portion, engaging the thread engaging portion of the instrument with the first part of the first thread in the cavity, and using the instrument to draw the first part of the first thread through the body of the sealing element.

The step of using the instrument to draw the first part of the first thread through the body of the sealing element may include the step of directing the instrument through the sealing element while maintaining the sealing element in sealing relationship fully around the instrument.

BRIEF DESCRIPTION OF THE DRAWINGS

FIG. 1 is an elevation view, partially in cross-section, of one form of system for facilitating the performance of a medical procedure, according to the present invention, and with a device/sealing element in an operative state relative to tissue bounding a cavity and with a sleeve and medical instrument extending through the device/sealing element and into the cavity;

FIG. 2 is a view as in FIG. 1 of a modified form of system for facilitating the performance of a medical procedure, according to the present invention, and with a thread maintaining the device/sealing element stably in the operative state relative to the tissue;

FIG. 3 is an elevation view of the system in FIG. 2 rotated through 90° from the view in FIG. 2;

FIG. 4 is a view as in FIG. 2 with a tying instrument being directed through the device/sealing element to engage a thread within the cavity bounded by the tissue;

FIG. 11 is an enlarged, plan view of the inventive device/sealing element;

FIG. 12 is an enlarged, elevation view of the inventive device/sealing element;

FIG. 13 is a view as in FIG. 12 with the device/sealing element rotated through 90° around a vertical axis from the view in FIG. 12;

FIG. 14 is an enlarged, bottom view of the inventive device/sealing element;

DETAILED DESCRIPTION OF THE DRAWINGS

Figure 5:
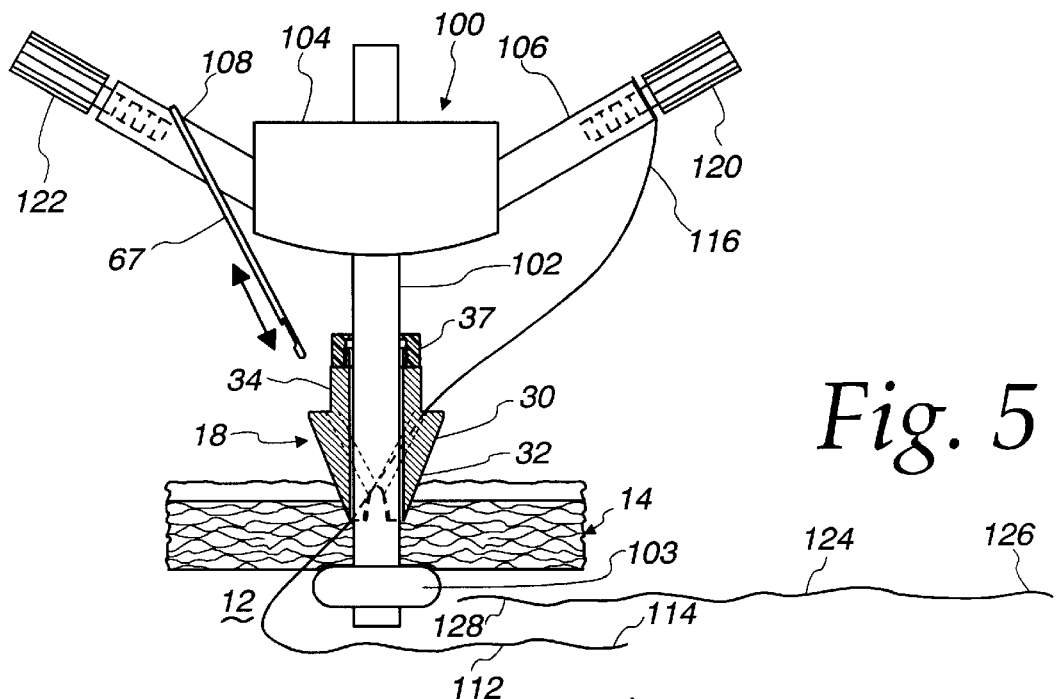
FIG. 5 is a view as in FIG. 4 with a part of the thread having been drawn through the device/sealing element.
Figure 6:
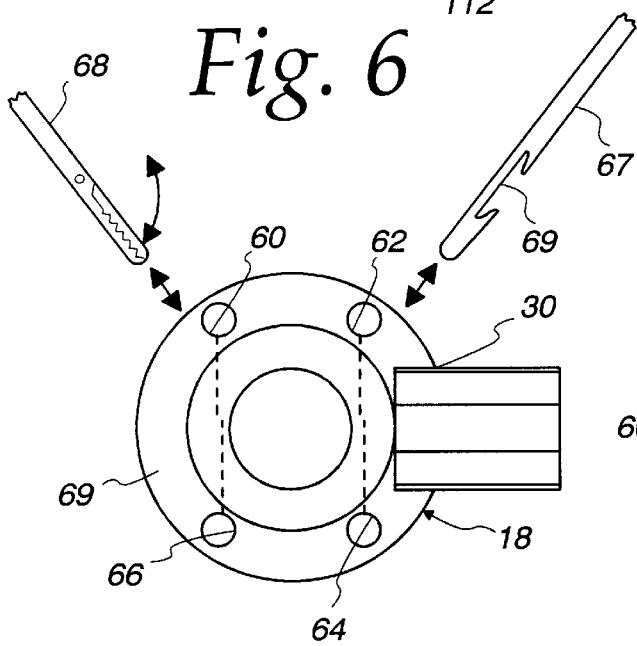
FIG. 6 is an enlarged, plan view of the inventive device/sealing element with different tying instruments being directed through passageways in the device/sealing element.
Figure 7:
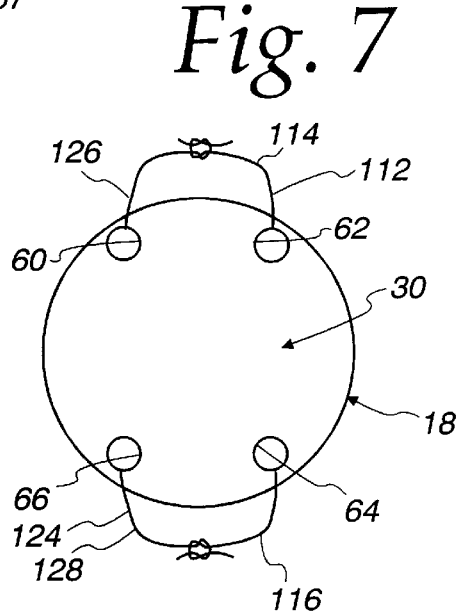
FIG. 7 is a schematic representation of the device/sealing element from the view as in FIG. 6 and showing one tying pattern for thread that is drawn through the device/sealing element.

In FIG. 1, a system, according to the present invention, is shown at 10, for performing a procedure within a cavity 12 bounded by a tissue 14. The procedure is carried out through an opening 16 in the tissue 14. In a typical laparoscopic procedure, the opening 16 is on the order of 6–12 mm to accommodate instruments routinely used in laparoscopic procedures.

The system 10 includes a device/sealing element 18 with a first opening/passageway 20 therethrough to accommodate a cylindrical sleeve/cannula 22. The sleeve/cannula 22 has an inlet end 24 with a resilient sealing element 26 and an outlet end 28.

With the device/sealing element 18 and sleeve/cannula 22 in a relative operative position as seen in FIG. 1 and the device/sealing element 18 in the operative state as also shown in FIG. 1, the inlet end 24 of the sleeve/cannula 22 resides externally of the tissue 14, with the outlet end 28 residing within the cavity 12 bounded by the tissue 14.

As seen in FIGS. 1 and 9–14, the device/sealing element 18 has a body 30 with a conical, external sealing surface 32. The body 30 has a neck 34 which closely surrounds the external surface 36 of the sleeve/cannula 22. A conventional, rubber seal 37 is press fit at the top of the neck 34 and closely embraces the sleeve/cannula 22. The bottom of the body 30 has an outlet opening 38 which closely receives the sleeve/cannula 22. In a preferred form, the opening/passageway 20 has a uniform diameter substantially fully between the inlet and outlet ends of the body 30. With the sleeve/cannula 22 and body 30 in the relative operative position, the device/sealing element 18 is slidable guidingly along the length of the sleeve/cannula 22. A hand operable set screw 40 is threaded through the neck 34 to against the sleeve/cannula 22. By tightening the set screw 40, the device/sealing element 18 can be fixed at any desired position along the length of the sleeve/cannula 22.

An inflatable bladder 42 surrounds the sleeve/cannula 22 adjacent to the outlet end 28 thereof. The bladder 42, in a deflated state, does not project significantly outwardly from the peripheral surface 36 of the sleeve/cannula 22. In an inflated state, as shown in FIG. 1, the bladder 42 defines an annular shoulder 44 surrounding the sleeve/cannula 22 which can be borne against the inwardly facing surface 46 of the tissue 14 as shown in FIG. 1.

To direct the sleeve/cannula 22 through the tissue 14, a sharpened trocar (not shown) is directed through the sleeve/cannula 22. The bladder 42 is deflated. The trocar guides the outlet end 28 of the sleeve/cannula 22 through the preformed tissue opening 16 to the FIG. 1 position. The bladder 42 is then inflated, after which the sleeve/cannula 22 is drawn upwardly to bear the bladder shoulder 44 sealingly against the tissue surface 46. The device/sealing element 18 is then slid downwardly along the sleeve/cannula 22 into the operative state wherein the outlet end of the sealing surface 32 on the body 30 compresses the tissue 14 so that a seal is established between the surface 32 and the tissue 14 fully around the opening 16. At the same time, the tissue 14 becomes firmly captive between the device/sealing element 18 and the bladder 42 so that the sleeve/cannula 22 is stably maintained in the FIG. 1 position on the tissue 14. This relationship is maintained by tightening the set screws 40.

Once the sleeve/cannula 22 and device/sealing element 18 are set up as in FIG. 1, a desired instrument can be directed through the sleeve/cannula 22 into the cavity 12. In this case, a forceps-type instrument 48 is shown having a working end 50 with relatively movable jaws 52, 54 that are operable through a remote actuator, shown schematically at 56 at a location externally of the cavity 12. The seal 26 surrounds the body 58 of the forceps 48 to prevent escape of gas from the cavity 12 as is typically used to distend the tissue 14 to provide an unobstructed working area at the outlet end 28 of the sleeve/cannula 22.

According to the invention, as seen in FIGS. 1 and 6–14, the body 30 of the device/sealing element 18 is provided with multiple, and in this case four, additional passageways 60, 62, 64, 66, each of which provides a guide path for an elongate, medical tying instrument. Two forms of a suitable medical tying instrument are shown at 67 and 68 in FIGS. 5 and 6. The instrument 67 has a conventional slot 69 which receives a suturing thread and can be used to either push or pull the thread through the tissue 12, depending upon which portion of the slot 69 is used. The instrument 68 has a conventional jawed construction. The particular configuration of the tying instrument is not critical to the present invention. Any medical tying instrument that can pass through the passageways 60, 62, 64, 66 into the cavity 12 with the system 10 in the FIG. 1 state can be employed.

In the embodiment shown, the passageways 60, 62, 64, 66 are substantially straight, with the central axes of the passageways 60, 62, 64, 66 being non-parallel. The passageways 60, 62, 64, 66 each have a diameter that is substantially less than the diameter of the opening/passageway 20. Exemplary passageway 60 extends through an upper annular surface 69 on the body 30 fully through the body 30 to an inverted, U-shaped cutout 70 adjacent to the bottom edge 72 of the body 30. As seen in FIG. 1, with the sleeve/cannula 22 and device/sealing element 18 in the relative operative position and the device/sealing element 18 in the operative state of FIG. 1, the outlet end 74 of the passageway 60 resides within, and preferably beneath, the outer skin layer 84 in the tissue 14 so that the central axis 86 of the passageway 60 passes through only a slight portion of the skin layer 84 and, more preferably, does not extend through the skin layer 84 at all. As a result, direction of one of the instruments 67, 68 through the passageway 60 causes the instrument 67, 68 to primarily or directly penetrate the layers 87 beneath the outer skin layer 84. The other passageways 62, 64, 66 are similarly configured and angled with respect to each other. Preferably the central axes of the passageways 60, 62, 64, 66 do not extend through the internal space 88 bounded by the sleeve/cannula 22.

Before describing the method of using the system 10, a modified form of system 100 as shown in FIGS. 2–5 will be described. The system 100 employs the device/sealing element 18, as previously described, and a sleeve/cannula 102 having an inflatable bladder 103 thereon. The sleeve/cannula 102 rigidly connects to an upper housing 104 which has two connecting arms 106, 108 projecting angularly away from the housing 104. This sleeve/cannula 102, housing 104, and connecting arm 106, 108 combination is shown in my U.S. Pat. No. 5,601,577, incorporated hereby by reference. An instrument shown schematically in FIG. 2 at 110, is directed through the housing 104, the sleeve/cannula 102, and into the cavity 12 in the same manner as the forceps 48 is directed through the sleeve/cannula 22 in FIG. 1. The device/sealing element 18 is fixed to the cannula 102 through the set screw 40 to maintain the sleeve/cannula 102 and device/sealing element 18 in the relative operative position in FIGS. 2–5.

The method of closing the tissue opening 16, according to the present invention, will now be described with reference to FIGS. 2–8, using the system 100. The system 10 is operable in essentially the same manner.

With the sleeve/cannula 102 and the device/sealing element 18 in the relative operative position and the device/sealing element 18 in the operative state of FIGS. 2–5, a suturing thread 112 is directed into the cavity 12. The thread 112 could be introduced into the cavity 12 before the system 100 is set up. Alternatively, using one of the instruments 67, 68, the thread 112 can be directed through one of the passageways 60, 62, 64, 66 with the system 100 set up. In FIG. 5, the thread 112 is directed through either of the passageways 64, 66. Thereafter, the instrument 67, 68 is directed through one of the passageways 60, 62 to engage the free end 114 of the thread 112 within the cavity 12 and draw the thread end 114 outwardly through the one of the passageways 60, 62.

The trailing end 116 of the thread 112 that remains outside of the cavity 12 is fixed to the arm 106 through a cap 120 which can be threaded into the connecting arm 106 to captively hold the thread end 116 thereagainst. The leading thread end 114 is then drawn taut and captively held against the other connecting arm 108 by threading a like cap 122 into the connecting arm 108. With this arrangement, the thread 112 serves to stabilize the sleeve/cannula 102 on the tissue 14. To add further stability, and also to facilitate closing of the tissue opening 16 as explained below, a separate thread 124 can be directed through the tissue 14 using the passageways 60, 62, 64, 66 not occupied by the thread 112 in the same manner as the thread 112. The ends 126, 128 of the thread 124 are secured to the connecting arms 106, 108 with the thread 124 drawn taut. The threads 112, 124 can cross each other as by extending through the openings 62, 66 or 60, 64 or remain uncrossed as by extending through the openings 60, 66 or 62, 64. Alternatively, the threads 112, 124 can extend through the openings 60, 62 or 64, 66.

With the system 100 set up as described above, the instrument 110, or any other desired instrument, can be positively controlled as the particular procedure is performed within the cavity 12. The threads 112, 124 not only stabilize the sleeve/cannula 102 but inherently rigidify the tissue 14 around the working area.

Figure 8:
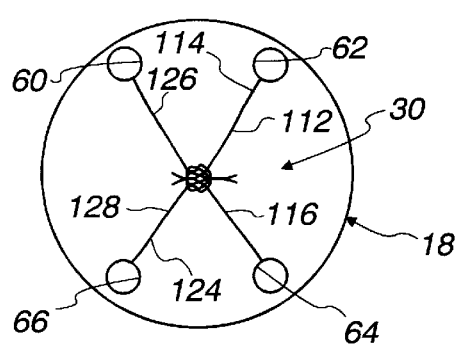
FIG. 8 is a view as in FIG. 7 showing another thread tying pattern.
Figure 9:
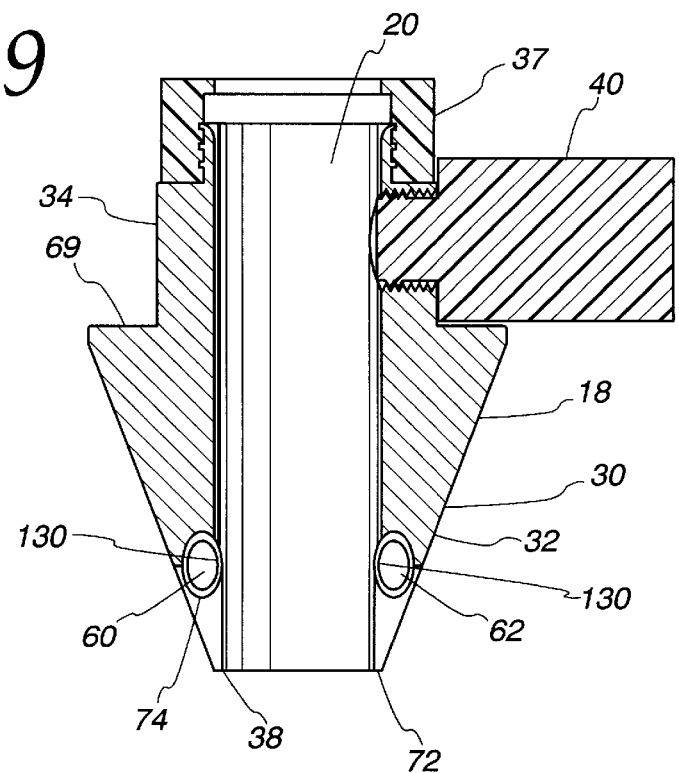
FIG. 9 is an enlarged, cross-sectional view of the inventive device/sealing element.
Figure 10:
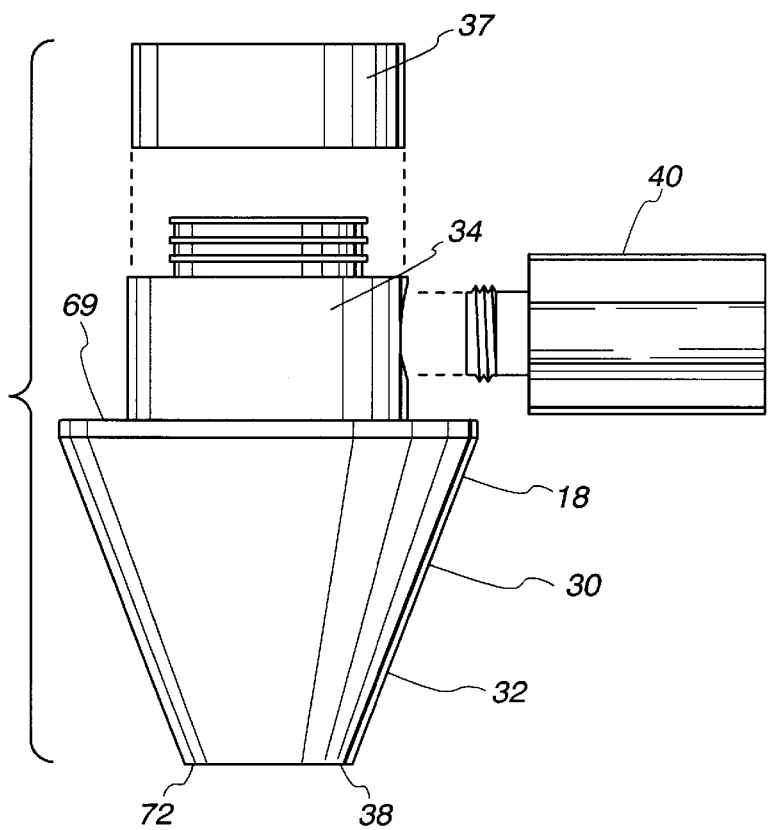
FIG. 10 is an enlarged, exploded, elevation view of the inventive device/sealing element.
Figure 15:
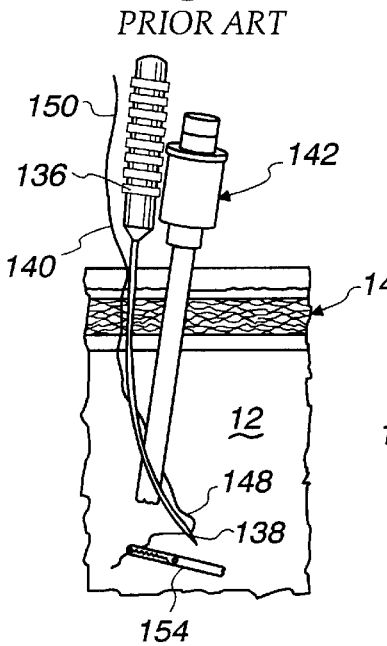
FIG. 15 is a schematic representation of a conventional suturing operation wherein a thread is directed by an instrument from externally of a tissue through the tissue and into a cavity.
Figure 16:
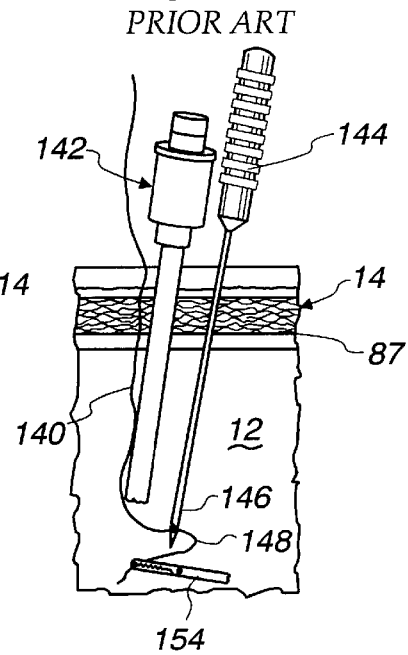
FIG. 16 is a view as in FIG. 15 wherein a separate instrument is used to engage and draw a portion of the thread in the cavity outwardly through the tissue.
Figure 17:
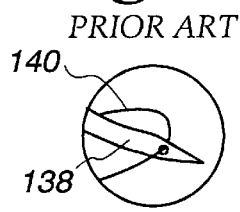
FIG. 17 is an enlarged, fragmentary view of a thread holding portion on the instrument in FIG. 15.
Figure 18:
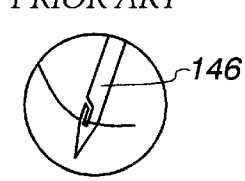
FIG. 18 is a view as in FIG. 17 of the thread holding portion on the instrument in FIG. 16.

Once the particular procedure is completed, the caps 120, 122 can be loosened to release the threads 112, 124 from the connecting arms 106, 108. The bladder 103 can then be deflated, allowing the cannula 102 and device/sealing element 18 to be separated from the tissue 14. The ends 114, 116, 126, 128 of the threads 112, 124 remain conveniently externally of the tissue 14 to be tied to each other in a manner to close the opening 16. The thread ends 114, 116, 126, 128 can be tied to each other in a variety of different manners to close the opening 16 beneath the skin layer 84. For example, the thread parts 114, 116 can be tied together as can the thread parts 126, 128, as shown in FIG. 8. Once combined, the thread parts 114, 116 and 126, 128 can be tied to each other as seen in FIG. 8. Alternatively, only the thread parts 114, 116 and the thread parts 126, 128 can be tied as in FIG. 7, or only the thread parts 116, 126 and 114, 124 can be tied. After the underlying tissue layers are closed, the skin 84 can be stapled or sutured to complete the procedure.

To prevent communication of pneumoperitoneum gas from the cavity 12 to externally of the tissue 14, a resilient seal/sleeve 130 (FIG. 9) can be provided in each of the passageways 60, 62, 64, 66 to closely embrace the tying instruments 67, 68 in the event that the body 30 is made from metal. Alternatively, the entire body, or a substantial portion thereof can be made from a sealing rubber material through which the passageways 60, 62, 64, 66 are formed.

Figure 19:
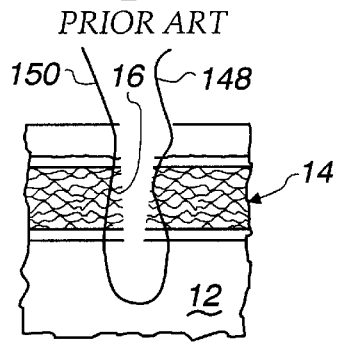
FIG. 19 is a cross-sectional view of a tissue wherein the thread is directed through the tissue into the cavity and outwardly from the cavity through the tissue around a tissue opening through the procedures shown in FIGS. 15 and 16.
Figure 20:
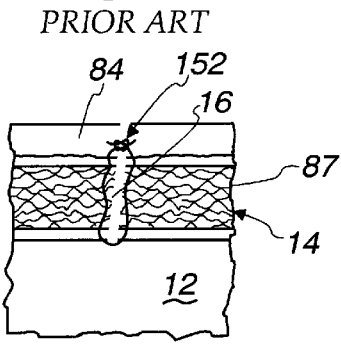
FIG. 20 is a view as in FIG. 19 with the thread tied to close the opening through the tissue.

FIGS. 15–20, a conventional method of closing an opening 16 in tissue 14 is shown. A first instrument 136 having a working end 138 to accept a thread 140 is directed through the tissue 14 adjacent to an operatively set up cannula 142. A second instrument 144 with a slotted working end 146 is directed through the tissue into the cavity 12 to pick up the leading end 148 of the thread 140 and is withdrawn to situate the leading end 148 externally of the tissue 14 adjacent to the trailing end 150 of the thread 140. The ends 148, 150 can then be tied at 152, as shown in FIGS. 19 and 20. A jawed instrument 154 can be directed into the cavity 12 to assist the transfer of the leading thread end 140 from the instrument 136 to the instrument 144. The thread 140 is not used to stabilize the cannula 142. Additionally, the upper tissue layer 84 must be peeled back to allow direction of the thread 140 into the underlying layers 87. Further, to avoid clashing between the instruments 136, 144 and the cannula 142, the thread may have to be directed through the tissue 14 at a greater than desired distance from the tissue opening 16.

The foregoing disclosure of specific embodiments is intended to be illustrative of the broad concepts comprehended by the invention.

I claim:

1. A device for facilitating the performance of a medical procedure in a cavity bounded by a tissue, said device comprising:
    a body having a first opening therethrough to define a first passageway for a medical instrument to be directed from externally of the cavity through an opening in the tissue to the cavity and an exposed surface that can be placed against the tissue around the opening therethrough with the device in an operative state relative to the tissue,
    the first passageway having a central axis,
    there being a second opening through the body to define a second passageway through which a tying instrument can be directed from externally of the tissue through the body and into the cavity bounded by the tissue,
    the second passageway having a central axis,
    wherein the first and second axes are non-parallel and non-perpendicular with respect to each other.

2. The device according to claim 1 wherein the first and second passageways do not intersect each other.

3. The device according to claim 1 wherein there is a third opening through the body defining a third passageway through which a tying instrument can be directed from externally of the tissue through the body and into the cavity bounded by the tissue.

4. The device according to claim 3 wherein the first, second, and third passageways do not intersect each other.

5. The device according to claim 4 wherein the third passageway has a central axis, the second and third passageways are substantially straight, and the central axes of the second and third passageways are non-parallel to each other.

6. In combination
    a) a device for facilitating the performance of a medical procedure in a cavity bounded by a tissue, said device comprising:
    a body having a first opening therethrough to define a first passageway for a medical instrument to be directed from externally of the cavity through an opening in the tissue to the cavity and an exposed surface that can be placed against the tissue around the opening therethrough with the device in an operative state relative to the tissue,
    there being a second opening through the body to define a second passageway through which a tying instrument can be directed from externally of the tissue through the body and into the cavity bounded by the tissue; and
    b) a sleeve which is extended into the first opening in the body.

7. In combination:
    a) a device for facilitating the performance of a medical procedure in a cavity bounded by a tissue, said device comprising:
    a body having a first opening therethrough to define a first passageway for a medical instrument to be directed from externally of the cavity through an opening in the tissue to the cavity and an exposed surface that can be placed against the tissue around the opening therethrough with the device in an operative state relative to the tissue,
    there being a second opening through the body to define a second passageway through which a tying instrument can be directed from externally of the tissue through the body and into the cavity bounded by the tissue; and
    b) a sleeve having an inlet end and an outlet end, the inlet end of the sleeve residing externally of the tissue and the outlet end of the sleeve residing within the cavity bounded by the tissue with the sleeve and body in a relative operative position and the device in the operative state.

8. In combination:
    a) a tissue bounding a cavity and having an opening therethrough in communication with the cavity;
    b) a device for facilitating the performance of a medical procedure in the cavity, said device comprising:
    a body having a first opening therethrough to define a first passageway for a medical instrument to be directed from externally of the cavity through the opening in the tissue to the cavity and an exposed surface that can be placed against the tissue around the opening therethrough with the device in an operative state relative to the tissue,
    there being a second opening through the body to define a second passageway through which a tying instrument can be directed from externally of the tissue through the body and into the cavity bounded by the tissue, wherein the external surface of the body is sealingly placed against the tissue around the tissue opening so that the first passageway is aligned with the tissue opening; and c) a medical instrument extending from externally of the tissue through one of the first and second passageways into the cavity.

9. The combination according to claim 8 wherein the medical instrument extends through the first passageway and the tissue opening into the cavity.

10. The combination according to claim 9 in combination with a sleeve that extends into the first passageway and the medical instrument extends through the sleeve.

11. The combination according to claim 9 in combination with a second instrument having a thread holding portion, said second instrument extending through the second passageway from externally of the tissue so that the thread holding portion of the second instrument resides within the cavity.

12. The combination according to claim 11 in combination with a suturing thread residing at least partially in the cavity with the thread holding portion of the second instrument holding a part of the suturing thread that is in the cavity.

13. The device for facilitating the performance of a medical procedure in a cavity bounded by a tissue, said device comprising:

a body having a first opening therethrough to define a first passageway for a medical instrument to be directed from externally of the cavity through an opening in the tissue to the cavity and an exposed surface that can be placed against the tissue around the opening therethrough with the device in an operative state relative to the tissue, there being a second opening through the body to define a second passageway through which a tying instrument can be directed from externally of the tissue through the body and into the cavity bounded by the tissue; and a resilient seal for the second passageway to block communication of gas from the cavity through the second passageway to externally of the cavity with the second instrument extending through the second passageway.

14. A method of closing an opening through a tissue bounding a cavity, said method comprising the steps of:

providing a sealing element having a body with an external surface;

placing the body of the sealing element against the tissue over the opening in the tissue;

directing a first thread into the cavity;

drawing a first part of the first thread from the cavity through the body of the sealing element and the tissue to externally of the tissue; and using the first part of the first thread to at least one of a) stabilize the sealing element on the tissue, and b) form a knot to at least partially close the opening in the tissue.

15. The method of closing an opening through a tissue according to claim 14 including the step drawing a second part of the first thread from the cavity through the body of the sealing element and the tissue to externally of the tissue and tying the first and second thread parts together to at least partially close the opening in the tissue.

16. The method of closing an opening through a tissue according to claim 14 including the steps of directing a second thread into the cavity, drawing a first part of the second thread from the cavity through the tissue to externally of the cavity, and tying the first parts of the first and second threads together to at least partially close the opening in the tissue.

17. The method of closing an opening through a tissue according to claim 14 including the steps of providing a medical instrument and directing the medical instrument through a first passageway through the body of the sealing element and the step of drawing a first part of the first thread from the cavity comprises the step of drawing a first part of the first thread through the body of the sealing element through a second passageway in the body of the sealing element that is independent from the first passageway.

18. The method of closing an opening through a tissue according to claim 14 including the step of providing a sleeve that extends into the body of the sealing element to allow a medical instrument to be directed through the sleeve and body of the sealing element into the cavity and the step of drawing a first part of the first thread through the body of the sealing element comprises the step of drawing a first part of the first thread through the body of the sealing element without drawing the first thread through the sleeve.

19. The method of closing an opening through a tissue according to claim 14 wherein the step of drawing a first part of the first thread through the body of the sealing element comprises the steps of providing an instrument with a thread engaging portion, engaging the thread engaging portion of the instrument with the first part of the first thread in the cavity and using the instrument to draw the first part of the first thread through the body of the sealing element.

20. The method of closing an opening through a tissue according to claim 19 wherein the step of using the instrument to draw the first part of the first thread through the body of the sealing element comprises the step of directing the instrument through the sealing element and withdrawing the instrument from the sealing element while maintaining the sealing element in sealing relationship fully around the instrument.

21. A device for facilitating the performance of a medical procedure in a cavity bounded by a tissue, said device comprising:

a body having a first opening therethrough to define a first passageway for a medical instrument to be directed from externally of the cavity through an opening in the tissue to the cavity and an exposed surface that can be placed against the tissue around the opening therethrough with the device in an operative state relative to the tissue, there being a second opening through the body to define a second passageway through which a tying instrument can be directed from externally of the tissue through the body and into the cavity bounded by the tissue, there being a third opening through the body to define a third passageway through which a tying instrument can be directed from externally of the tissue through the body and into the cavity bounded by the tissue, the second and third passageways each having a central axis, the axes of the second and third passageways being non-parallel and non-perpendicular with respect to each other.

22. The device according to claim 21 wherein the first, second, and third passageways each have a diameter and the diameter of at least one of the second and third passageways is substantially less than the diameter of the first passageway.

23. The device according to claim 22 wherein the diameter of each of the second and third passageways is substantially less than the diameter of the first passageway.

* * * * *